United States Patent
Sheth et al.

(10) Patent No.: US 10,605,736 B2
(45) Date of Patent: Mar. 31, 2020

(54) OPTICAL PATHOLOGY SYSTEMS AND METHODS

(71) Applicant: The General Hospital Corporation, Boston, MA (US)

(72) Inventors: Rahul Sheth, Houston, TX (US); Umar Mahmood, Winchester, MA (US); Anthony Samir, Newton, MA (US)

(73) Assignee: The General Hospital Corporation, Boston, MA (US)

(*) Notice: Subject to any disclaimer, the term of this patent is extended or adjusted under 35 U.S.C. 154(b) by 1147 days.

(21) Appl. No.: 14/799,135

(22) Filed: Jul. 14, 2015

(65) Prior Publication Data
US 2016/0033414 A1   Feb. 4, 2016

Related U.S. Application Data

(60) Provisional application No. 62/031,350, filed on Jul. 31, 2014.

(51) Int. Cl.
| | |
|---|---|
| *A61B 5/00* | (2006.01) |
| *G01N 21/64* | (2006.01) |
| *A61B 10/02* | (2006.01) |
| *A61B 8/08* | (2006.01) |
| *G01J 1/42* | (2006.01) |
| *G01J 1/02* | (2006.01) |
| *G01N 21/76* | (2006.01) |
| *A61B 6/03* | (2006.01) |

(52) U.S. Cl.
CPC ....... *G01N 21/6486* (2013.01); *A61B 8/0841* (2013.01); *A61B 10/02* (2013.01); *G01J 1/0223* (2013.01); *G01J 1/42* (2013.01); *G01N 21/6428* (2013.01); *G01N 21/763* (2013.01); *A61B 6/032* (2013.01); *G01N 2201/062* (2013.01)

(58) Field of Classification Search
None
See application file for complete search history.

(56) References Cited

U.S. PATENT DOCUMENTS

| | | | |
|---|---|---|---|
| 2004/0207625 A1* | 10/2004 | Griffin | A61B 5/0059 345/440 |
| 2009/0051901 A1* | 2/2009 | Shen | B29D 11/00365 356/73 |

(Continued)

OTHER PUBLICATIONS

Bertolotti, J., et al. "Non-invasive imaging through opaque scattering layers." Nature 491.7423 (2012): 232.

(Continued)

*Primary Examiner* — Joel F Brutus
(74) *Attorney, Agent, or Firm* — Quarles & Brady LLP

(57) ABSTRACT

An optical imaging method for analyzing an ex vivo tissue sample of a subject is provided. The method includes obtaining the ex vivo tissue sample, preparing the ex vivo tissue sample onto a sample receptacle of an optical imaging system, and emitting excitation light toward the ex vivo tissue sample. The method also includes acquiring imaging data of light emitted by the ex vivo tissue sample in response to the excitation light, analyzing the imaging data to determine whether the ex vivo tissue sample contains pathologic tissue, and generating an output indicating to an operator whether the ex vivo tissue sample contains pathologic tissue.

8 Claims, 4 Drawing Sheets

(56) References Cited

U.S. PATENT DOCUMENTS

| | | | |
|---|---|---|---|
| 2010/0022866 A1* | 1/2010 | Feke | A61B 5/0059 600/407 |
| 2012/0302892 A1* | 11/2012 | Lue | A61B 5/0071 600/476 |

OTHER PUBLICATIONS

De Lope Cr, et al. "Management of HCC." Journal of hepatology 56 (2012): S75-S87.

Funovics Ma, et al. Catheter-based in vivo imaging of enzyme activity and gene expression: feasibility study in mice. Radiology. Jun. 2004 1;231(3):659-66.

Funovics Ma, et al. Simultaneous fluorescence imaging of protease expression and vascularity during murine colonoscopy for colonic lesion characterization. Gastrointest Endosc. Oct. 1, 2006; 64(4):589-97.

Goetz M, et al. In vivo molecular imaging of colorectal cancer with confocal endomicroscopy by targeting epidermal growth factor receptor. Gastroenterology 2010;138(2):435-446.

Hsiung Pl, et al. Detection of colonic dysplasia in vivo using a targeted heptapeptide and confocal microendoscopy. Nat Med 2008;14(4):454-458.

Ishizawa T, et al. Real-time identification of liver cancers by using indocyanine green fluorescent imaging. Cancer 2009;115(11):2491-2504.

Ishizawa, T., et al. "Mechanistic background and clinical applications of indocyanine green fluorescence imaging of hepatocellular carcinoma." Annals of surgical oncology 21.2 (2014): 440-448.

Kar S, et al. Percutaneous optical imaging system to track reporter gene expression from vasculatures in vivo. Journal of biomedical optics. May 2006;11(3):34008.

Katz, Ori, et al. "Non-invasive real-time imaging through scattering layers and around corners via speckle correlations." arXiv preprint arXiv:1403.3316 (2014).

Kimura T, et al. Infrared fluorescence endoscopy for the diagnosis of superficial gastric tumors. Gastrointest Endosc 2007;66(1):37-43.

Kokudo N, et al. Clinical application of fluorescence imaging of liver cancer using indocyanine green. Liver Cancer 2012;1(1):15-21.

Lencioni R, et al. Modified Recist (mRECIST) assessment for hepatocellular carcinoma. Semin Liver Dis 2010;30 (1):52-60.

Ma X, et al. Success of image-guided biopsy for small (=3 cm) focal liver lesions in cirrhotic and noncirrhotic Individuals. J Vasc Interv Radiol 2010;21(10):1539-1547.

Morita Y, et al. Detection of hepatocellular carcinomas with near-infrared fluorescence imaging using indocyanine green: its usefulness and limitation. Int J Clin Oncol 2013;18(2): 232-241.

Obuchowski Na. Receiver operating characteristic curves and their use in radiology. Radiology. Oct. 2003;229(1):3-8.

Raabe A, et al. Near-infrared indocyanine green video angiography: a new method for intraoperative assessment of vascular flow. Neurosurgery2003;52(1):132-139.

Regillo Cd. The present role of indocyanine green angiography in ophthalmology. Curr Opin Ophthalmol 1999;10 (3):189-196.

Sarantopoulos A, et al. Optical and opto-acoustic interventional imaging. Ann Biomed Eng. Feb. 2012;40(2):346-66.

Schaafsma Be, et al. The clinical use of indocyanine green as a near-infrared fluorescent contrast agent for image-guided oncologic surgery. J Surg Oncol 2011;104(3):323-332.

Sheth Ra, et al. Improved detection of ovarian cancer metastases by intraoperative quantitative fluorescence protease imaging in a preclinical model. Gynecologic Oncology. Mar. 2009;112(3):616-22.

Sheth Ra, et al. In vivo optical molecular imaging of matrix metalloproteinase activity in abdominal aortic aneurysms correlates with treatment effects on growth rate. Atherosclerosis 2010;212(1):181-187.

Sheth Ra, et al. Real-time multichannel imaging framework for endoscopy, catheters, and fixed geometry intraoperative systems. Mol Imaging 2007;6(3):147-155.

Sheth Ra, et al. "Evaluation and clinically relevant applications of a fluorescent imaging analog to fluorodeoxyglucose positron emission tomography." Journal of biomedical optics 14.6 (2009): 064014.

Sheth Ra, et al. Interventional optical molecular imaging guidance during percutaneous biopsy. Radiology2014;271 (3):770-777.

Sheth, R A., et al. "Quantitative endovascular fluorescence-based molecular imaging through blood of arterial wall Inflammation." Radiology 251.3 (2009): 813-821.

Stattaus J, et al. CT-guided biopsy of small liver lesions: visibility, artifacts, and corresponding diagnostic accuracy. Cardiovasc Intervent Radiol2007;30(5):928-935.

Stummer W, et al. Fluorescence-guided surgery with 5-aminolevulinic acid for resection of malignant glioma: a randomised controlled multicentre phase III trial. Lancet Oncol 2006;7(5):392-401.

Taruttis a, et al. Translational optical imaging. American Journal of Roentgenology. Aug. 2012;199(2):263-71.

Upadhyay R, et al. Quantitative real-time catheterbased fluorescence molecular imaging in mice. Radiology 2007;245(2):523-531.

Van Der Vorst Jr, et al. Near-infrared fluorescence imaging of liver metastases in rats using indocyanine green. Surg Res 2012;174(2):266-271. J.

Van Der Vorst Jr, et al. Near-infrared fluorescence-guided resection of colorectal liver metastases. Cancer2013;119(18):3411-3418.

Yang X. Interventional molecular imaging. Radiology. Mar. 2010;254(3):651-4.

Yokoyama N, et al. Real-time detection of hepatic micrometastases from pancreatic cancer by intraoperative fluorescence imaging: preliminary results of a prospective study. Cancer 2012; 118(11):2813-2819.

\* cited by examiner

OPTICAL PATHOLOGY SYSTEMS AND METHODS

CROSS-REFERENCE TO RELATED APPLICATIONS

This application is based on, claims priority to, and incorporates herein by reference in its entirety, U.S. Provisional Patent Application Ser. No. 62/031,350, filed on Jul. 31, 2014, and entitled "Fluorescent Pathology Systems and Methods."

BACKGROUND

Over the past two decades, improved cross-sectional diagnostic imaging techniques have resulted in earlier detection of abnormalities throughout the body. While such non-invasive detection is useful, however, the majority of focal abnormal lesions do not have specific imaging characteristics. For example, lesions smaller than 3 centimeters (cm) often lack specific features to allow reliable noninvasive characterization. Thus, biopsies of focal lesions are often necessary to establish tissue diagnosis of primary or metastatic hepatic malignancy, as well as to perform genotype analysis. Today, percutaneous interventions on focal lesions are among the most commonly performed procedures in Interventional Radiology.

Focal lesion core biopsies are predominantly performed with computed tomography (CT) or ultrasound (US) guidance. However, small lesions can pose several challenges using these techniques. Lesions which are seen on other modalities, such as magnetic resonance imaging (MRI), are sometimes not visible when using CT or US guidance. Alternatively, when the lesion is visible with CT, the biopsy needle introduces beam-hardening artifacts that may render the lesion difficult to see at the critical moment when the needle is in the lesion's vicinity. Furthermore, operator confidence in accurate needle placement using conventional CT or US guidance for biopsies and ablations decreases as target lesions decrease in size. For example, in a study having specialized attending physicians performing liver biopsies, the negative predictive value (NPV) of biopsy for liver lesions less than 3 cm was 72%. Therefore, over a quarter of liver lesions less than 3 cm that had negative biopsies were ultimately proven to be cancerous. It can be reasoned that in a broader community having generalists performing the liver biopsies, the rate of incorrect benign diagnoses would increase.

In light of the above challenges, biopsies are not considered a "perfect" test. In particular, a negative biopsy does not exclude a cancer diagnosis due to the potential for sampling errors. These sampling errors are often caused by: (1) a targeting failure where the core biopsy needle misses the lesion; (2) a sampling failure where the core biopsy needle intersects the lesion, but does not obtain sufficient malignant tissue; or (3) a tumor visualization failure where the tissue section reviewed by a pathologist does not pass through malignancy in the biopsy specimen. Because of these sampling errors, and a present lack of technology for quickly assessing biopsy adequacy, false negative cancer biopsy is very common in clinical cancer care. These errors result in delayed treatment, repeat biopsy procedures, higher costs, increased patient anxiety, and higher risk of biopsy complications.

Various attempts have been made to reduce the rate of false negative biopsy. For example, some institutions perform fine needle aspiration in addition to core biopsy, and then obtain cytologic "wet reads" of fine needle aspirates while the patient is still on the procedure table. This additional step requires on-site cytology specialist expertise, is not widely available, adds considerable procedure and sedation time, cost, and inconvenience, and does not always predict the final biopsy result. Furthermore, cytologic assessment of fine needle aspirate adequacy does not necessarily imply that core biopsy samples will be adequate for the tumor subtyping and genetic analyses necessary to correctly select personalized cancer therapies. Improved image guidance techniques, such as MRI-guided or fusion PET-CT guided biopsies, have also been developed, but these approaches, beyond the added time and cost, are not widely available.

Therefore, there exists a clinical need for a rapid point-of-care technology to assess core biopsy adequacy in a biopsy suite, prior to specimen submission for histopathologic and genetic examinations.

SUMMARY

The present disclosure overcomes the above and other drawbacks by providing systems and methods for non-destructively detecting pathologic tissue in biopsy specimens ex vivo by bed-side optical measurement.

According to one aspect of the disclosure, a three-dimensional optical pathology system for analyzing an ex vivo tissue sample is provided. The system includes a scaffold defining a hollow central chamber and two outlet channels, where the hollow central chamber is configured to receive the ex vivo tissue sample. The system also includes a plurality of excitation sources positioned along the scaffold and configured to emit light into the hollow central chamber, a camera positioned at each outlet channel and configured to acquire imaging data following light emission into the hollow central chamber, and a computer in communication with the plurality of excitation source and the cameras. The computer includes a processer configured to activate the excitation sources, collect the imaging data from the cameras, analyze the imaging data to distinguish pathologic tissue from non-pathologic tissue within the ex vivo tissue sample and determine a volumetric measurement of pathologic tissue within the ex vivo tissue sample, and display an indication of the volumetric measurement.

According to another aspect of the disclosure, an optical imaging method for analyzing an ex vivo tissue sample of a subject is provided. The method includes obtaining the ex vivo tissue sample, preparing the ex vivo tissue sample onto a sample receptacle of an optical imaging system, and emitting excitation light toward the ex vivo tissue sample. The method also includes acquiring imaging data of light emitted by the ex vivo tissue sample in response to the excitation light, analyzing the imaging data to determine whether the ex vivo tissue sample contains pathologic tissue, and generating an output indicating to an operator whether the ex vivo tissue sample contains pathologic tissue.

According to yet another aspect of the disclosure, an optical pathology system for analyzing an ex vivo tissue sample is provided. The system includes a sampling stage configured to receive the ex vivo tissue sample and an excitation source configured to emit excitation light toward the ex vivo tissue sample, wherein the excitation light causes pathologic tissue to emit different light than non-pathologic tissue. The emitted light may be generated by a variety of methods, including but not limited to fluorescence, autofluorescence, bioluminescence, Cerenkov luminescence. The system also includes a camera configured to acquire imaging data following light emission toward the ex vivo tissue sample and a computer in communication with the excitation source and the camera. The computer includes a processer configured to activate the excitation source to deliver the light to the ex vivo tissue sample, collect the imaging data from the camera, analyze the imaging data to distinguish pathologic tissue from non-pathologic tissue within the ex vivo tissue sample, and display an output indicating whether the ex vivo tissue sample contains pathologic tissue.

The foregoing and other advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present disclosure provides a point-of-care imaging system to evaluate core biopsy samples intra-procedurally. More specifically, the system uses optical molecular imaging (OMI) to improve sampling accuracy during interventional radiology (IR) procedures. Used in conjunction with optical imaging agents that target pathologic tissue, the system can be used in the procedure suite to measure light intensity of obtained core biopsy specimens (i.e., ex vivo tissue samples). This real-time assessment allows an operator to rapidly determine whether the specimens contain adequate pathologic tissue and, as a result, whether retargeting and/or additional tissue samples are necessary during the initial biopsy procedure. This intraprocedural knowledge of biopsy adequacy provided by the system can lower the number of false negative core biopsy procedures, reducing the need for repeat biopsy procedures and avoiding needless delays in care.

Figure 1:
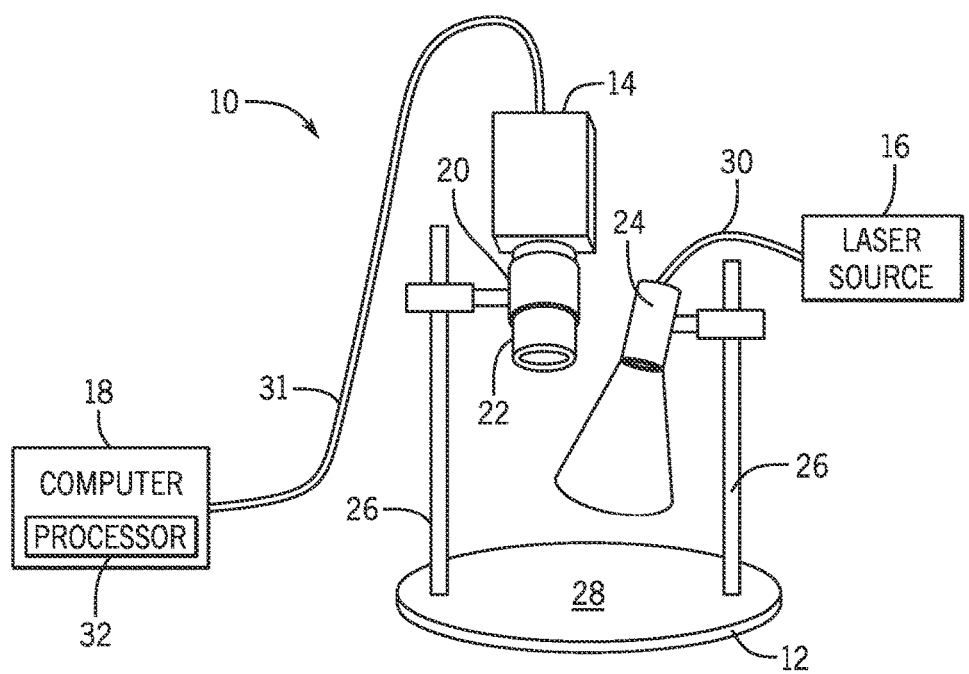
FIG. 1 is a schematic view of a two-dimensional optical pathology system according to one aspect of the disclosure.

FIG. 1 illustrates a two-dimensional optical pathology system 10 according to one aspect of the disclosure. Generally, the system 10 can include a sample stage 12, a camera 14, an excitation source (which may be a laser) 16, and a computer 18. The system 10 can also include a bandpass filter 20 and a zoom lens 22 coupled to the camera 14, a beam expander 24 coupled to the excitation source 16, and one or more frame elements 26 configured to position the camera 14 (specifically, the zoom lens 22) and the excitation source 16 (specifically, the beam expander 24) with respect to the sample stage 12.

The sample stage 12 can form part of a sample area or receptacle 28 sized to accommodate a biopsy sample (e.g., in a cuvette or on a slide, not shown), and the camera 14 and the excitation source 16 can be positioned by the frame elements 26 to image and emit light, respectively, toward the sample area 28. The system 10 can be a substantially portable "table-top" device and can be sized, for example, to fit on a rolling cart (not shown) to enable movement of the system 10 between procedure suites. In one configuration, the sample stage 12 can be about 250 millimeters (mm) by about 200 mm by about 70 mm.

In some configurations, the system 10 can have a substantially modular design. For example, a variety of cameras 14 and excitation sources 16 can be interchangeable based on the particular application of the system 10. Also, the camera 14 and the excitation source 16 can be removably coupled to the computer 18 so that the system 10 can be used with different computers 18 in different procedure suites.

As discussed above, the system 10 can be used in conjunction with an optical imaging agent to perform OMI of tissue. The excitation source 16 can emit a specific wavelength based on the optical imaging agent used. For example, in one configuration, the excitation source 16 may be a near-infrared (NIR) laser (such as a 450 mW, 785 nm laser) to be used with optical imaging agents that emit light under that range (e.g., via fluorescence, autofluorescence, bioluminescence, Cerenkov luminescence, etc.). The excitation source 16 can be coupled to the beam expander 24, e.g., through a fiber-optic cable 30, so that activating the excitation source 16 causes excitation light to be emitted through the beam expander 24. The beam expander 24 can provide uniform flood lighting onto the sample area 28 and, more specifically, on a biopsy sample placed on the sample area 28.

The camera 14 can be configured to capture images of the sample area 28 and, thus, can capture the resulting light photons from a biopsy sample following excitation light emission by the excitation source 16. In particular, light emitted by a biopsy sample can be collected by the zoom lens 22, such as a close focus video zoom lens. The bandpass filter 20 can be positioned between the camera 14 and the zoom lens 22 so that any excitation light from the excitation source 16 that is collected by the zoom lens 22 (e.g., after reflecting off the biopsy sample or sample stage 12) can be filtered before reaching the camera 14. The camera 14 can thus image the filtered light emitted by the biopsy sample. In some configurations, the camera 14 can be a charge-coupled device (CCD) camera, configured to acquire high-temporal and high-spatial resolution images in real time (such as 12-bit images). Additionally, in some configurations, the camera 14 may be optimized to the specific wavelength range as the excitation source 16 (such as NIR).

The computer 18 can communicate with the excitation source 16 and the camera 14 (or other image collection hardware) via cable connections 31. The computer 18 can control, for example, camera, light emission, and image display functions. More specifically, each computer 18 used with the system 10 can include a processor 32 configured to activate the excitation source 16, collect imaging data from the camera 14, analyze the imaging data, display the imaging data or outputs indicative of the analysis, and/or perform other operations (e.g., by executing a software program stored on the computer 18).

With respect to imaging, OMI encompasses a vast array of imaging modalities, but generally has features such as high spatial resolution, real-time image display, and highly sensitive imaging agents. Different optical imaging agents target different regions and/or pathologies, and generally localize at such pathologies with high sensitivity and target-to-background ratios. In other words, an optical imaging agent acts as a "molecular beacon" for pathologic tissue and will concentrate within the pathologic tissue while passing through surrounding healthy tissue. Thus, an optical imaging agent may be selected for a procedure based on the agent's properties relative to a targeted pathologic tissue. Pathologic tissue may include, but is not limited to, tumors, infectious tissue, and/or inflammatory tissue. Additionally, in some cases, benign and malignant lesions have significantly different imaging agent uptake and, thus, malignant lesions can be differentiated from benign lesions. Furthermore, for some tissues, endogenous fluorophores allow for differentiation between normal and abnormal tissue using optical imaging without requiring the administration of an exogenous imaging agent.

Figure 2:
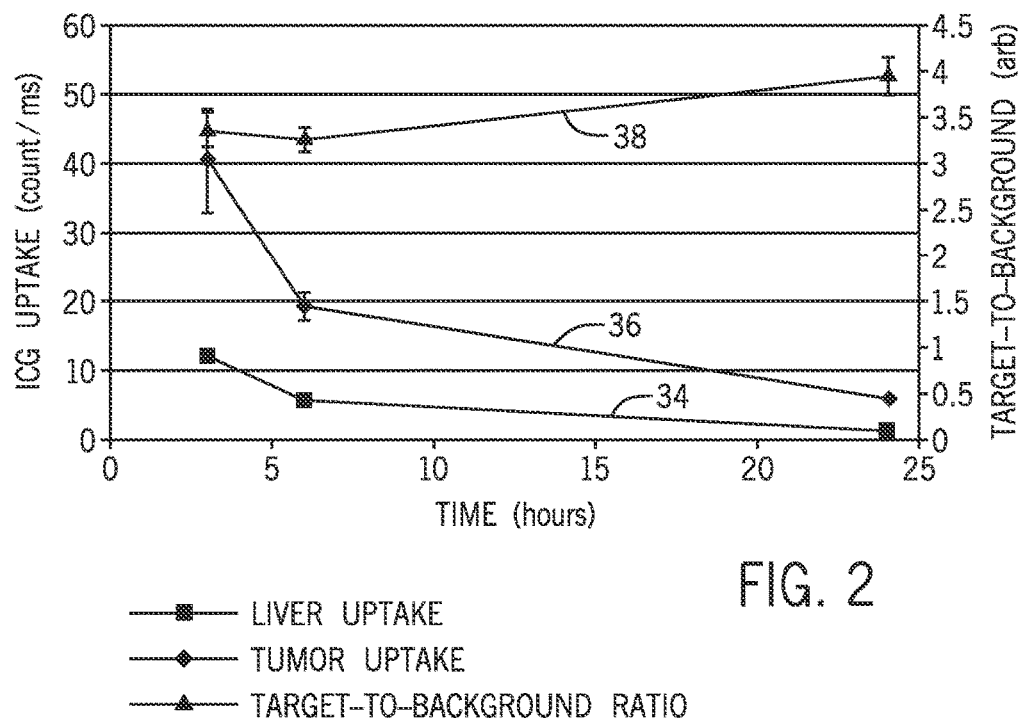
FIG. 2 is a graph illustrating optical imaging agent uptake over time in healthy liver tissue and tumor tissue, and target-to-background ratios of light measurements over time of the healthy liver tissue and tumor tissue.

Indocynanine green (ICG) is a clinically approved optical imaging agent that fluoresces in the near-infrared (NIR) range and localizes to hepatocellular carcinoma, hepatic metastatic disease, and non-malignant pathologic tissues (generally 24-72 hours after injection) with high target-to-background ratios (TBRs). Thus, upon administration of ICG to a patient with either pathology, the pathologic tissue will fluoresce during OMI with NIR light while surrounding healthy tissue will not fluoresce (or will minimally fluoresce compared to the pathologic tissue), providing a high target-to-background, or pathologic tissue-to-healthy tissue, ratio. In particular, FIG. 2 illustrates ICG uptake over time of healthy liver tissue 34 and a liver tumor 36, as well as TBRs 38 comparing fluorescence of the healthy tissue and the tumor tissue over time. As shown in FIG. 2, there is markedly less ICG uptake in healthy tissue 34 compared to pathologic tissue 36, resulting in high TBRs 38. As a result, the system 10 can be used to measure ICG fluorescence intensity within core biopsy samples, and samples containing pathologic tissue will have significantly higher fluorescence intensity (i.e., "bright spots") following ICG administration than normal or cirrhotic liver parenchyma. Thus, the system 10 can differentiate between core biopsy samples consisting of hepatic parenchyma and those containing focal lesions with, in some configurations, greater than 90% accuracy.

Figure 3:
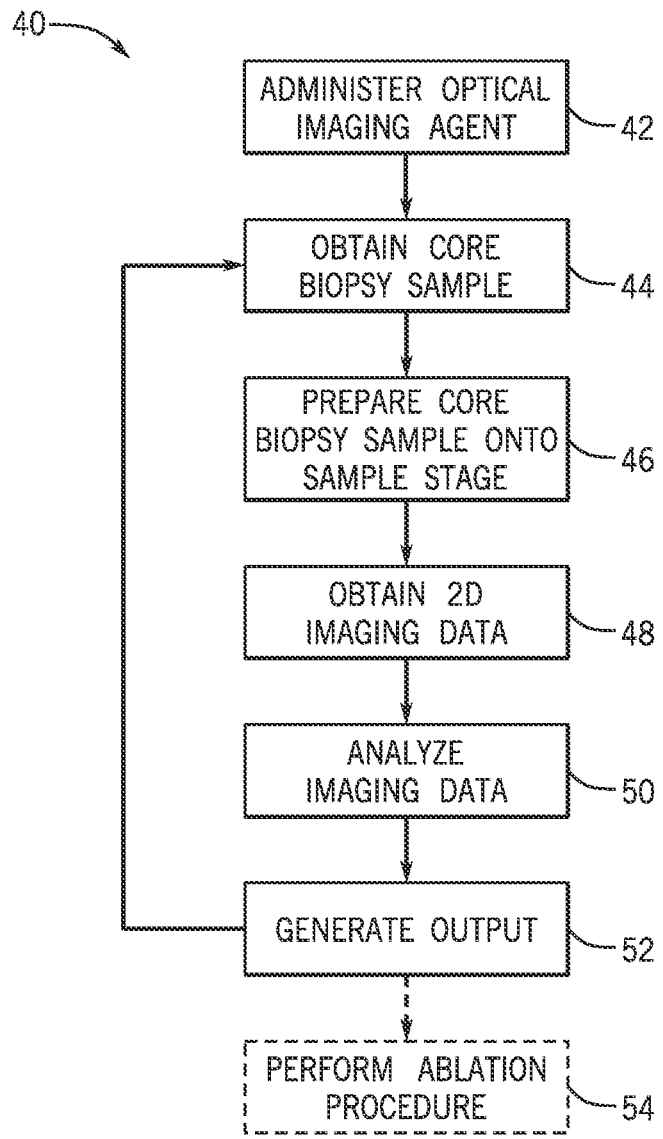
FIG. 3 illustrates a two-dimensional point-of-care imaging method according to one aspect of the disclosure.

In light of the above, an interventionalist can use the system to observe "bright spots" within collected images, indicating pathologies specific to the optical imaging agent. For example, FIG. 3 illustrates a two-dimensional point-of-care imaging method 40 according to one aspect of the disclosure, using the system 10. Generally, the method 40 includes administering an optical imaging agent to a subject (process block 42) and obtaining a core biopsy sample (process block 44). The extracted biopsy sample is then placed on the sample stage 12 (process block 46). The method 40 also includes obtaining imaging data of the biopsy sample (process block 48) then analyzing the imaging data (process block 50). Once the analysis is completed, an output indicative of the analysis is generated (process block 52). The method (that is, process blocks 44-52) may be repeated for multiple biopsy samples. Additionally, in some configurations, following output generation at process block 52, an operator may perform an ablation procedure at an area from where the core biopsy sample was collected (process block 54).

More specifically, process block 42 includes administering an optical imaging agent to a subject and waiting for the optical imaging agent to reach the target pathologic tissue. In some configurations, this waiting period may take minutes, hours, or days. Additionally, in configurations where pathologic tissue fluoresces or emits light differently than normal tissue without the addition of an optical imaging agent, this step may be eliminated. At process block 44, a biopsy sample is obtained, for example using US or CT guidance. At process block 46, the biopsy can be extracted from the biopsy needle and prepared in a cuvette or on a slide, for example, with a fixative solution, then placed on the sample area 28.

At process block 48, the computer 18 operates the excitation source 16 and the camera 14 to collect two-dimensional imaging data of the biopsy sample. Two-dimensional imaging data may refer to data collected from single angle. For example, an operator can provide input to the computer 18, directing the computer 18 to initiate imaging data collection. In response to this input, the computer 18 operates the excitation source 16 to emit excitation light toward the sample and then operates the camera 14 to collect imaging data of light emitted from the sample in response to the excitation light. For example, the sample may generate light via fluorescence, autofluorescence, bioluminescence, Cerenkov luminesce or other light generation methods.

In some configurations, the imaging data can include raw imaging data from the camera 14, or processed imaging data, such as an optical intensity measurement. For example, optical intensity measurements are measured by drawing a region of interest within a collected projected 12-bit image of the sample and calculating a mean pixel intensity of the region of interest (e.g., using an image analysis software package). Additionally, the optical intensity can be normalized by dividing the mean pixel intensity by the exposure time of the image. Normalized intensities can allow comparison between images with varying exposure times. In some configurations, a maximum optical intensity from the region of interest is also determined. Maximum optical intensity measurements may be helpful when biopsy samples include different types of tissue, such as healthy tissue, pathologic tissue, and/or necrotic tissue (which may include pathologic tissue, but does not release light). On the other hand, in some configurations, mean pixel intensities may better account for variables that affect maximum intensity, such as imaging agent concentration, sample thickness, pathologic tissue distribution, and distance between pathologic tissue and camera. In one configuration, the optical intensity is fluorescence intensity.

Additionally, in some configurations, image processing techniques may be applied to the imaging data, including scatter reduction techniques (such as angular 'memory-effect' for speckle correlations and an autocorrelation method). In some configurations, the computer 18 may display an image of the tissue, a numerical optical measurement, and/or a status symbol indicating that the measurement was taken. Additionally, imaging data can be stored on the computer 18 or other appropriate medium so that the imaging data can be later retrieved and analyzed.

At process block 50, the imaging data is analyzed by the computer 18 (e.g., via a specific software program) and/or by an operator (such as an interventional radiologist or surgeon). The purpose of the analysis at process block 60 is to determine whether the imaging data is sufficient, that is, whether the imaging data indicates presence of pathologic tissue in the biopsy sample. Analysis at process block 60 can include visual analysis of images (e.g., for brightness) and/or numerical analysis of optical measurement data to distinguish pathologic tissue from non-pathologic tissue. In some configurations, analysis may include comparing imaging data, such as mean or maximum optical intensity, to a stored threshold intensity. For example, intensities below the threshold intensity indicate non-pathologic tissue and intensities above the threshold intensity indicate pathologic tissue. In some configurations, multiple threshold stored intensities may be used and correlated with known histologic diagnoses. Such threshold intensities may be pre-determined based on scientific data.

At process block 52, the computer 18 may generate and display one or more outputs of the analysis, such as numerical optical measurements, status symbols indicating that the measurement is sufficient or insufficient (e.g., pathologic or non-pathologic), and/or potential histologies.

The method 40 can provide real-time guidance concerning whether additional samples should be acquired. In particular, process blocks 44-52 may be repeated to obtain multiple biopsy samples from the same or a new biopsy needle position based on the output generated at process block 52. In some configurations, while imaging data collection takes up to 3 seconds per sample, the method 40 may add less than five minutes to a conventional core biopsy procedure. Furthermore, the generated output at process block 52 can guide a pathologist in deciding where to obtain sections within a core biopsy sample, providing a useful intraoperative analysis of pathologic tissue, including frozen-section specimens. In some configurations, following output generation at process block 52, an operator can use the output to determine which parts of the biopsy sample contains pathologic tissue, then perform subsequent microscopic analysis in those areas (thus making the analysis more efficient by only focusing on pathologic tissue).

Additionally, in some configurations, following output generation at process block 52, an operator can perform an ablation procedure at process block 54. For example, the method 40 can be used to determine proper introducer needle position at or within the pathologic tissue. When output indicates that a sample taken at that needle position contains pathologic tissue, an ablation probe, such as a microwave antenna, can be inserted through the introducer needle to perform, for example, microwave or radiofrequency ablation. The method 40 (or at least process blocks 44-54) may be repeated to ensure the pathologic tissue, in its entirety, is sufficiently burned via the ablation procedure.

Figure 4:
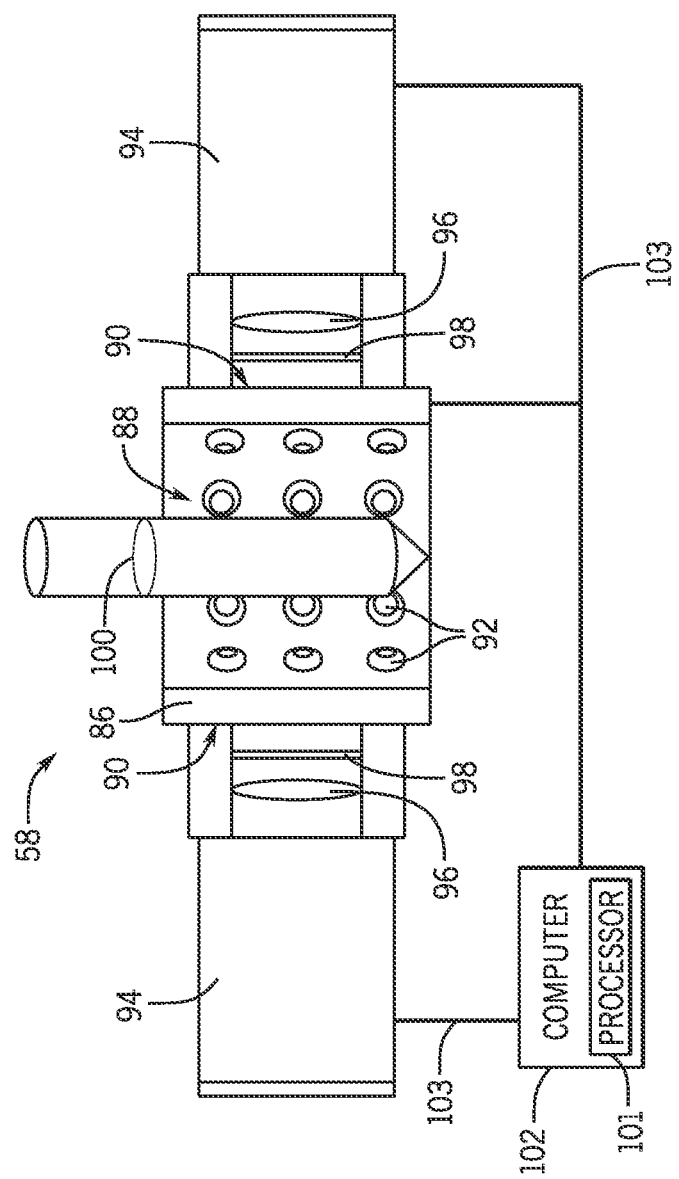
FIG. 4 is a schematic view of a three-dimensional optical pathology system according to another aspect of the disclosure.

The above system 10 and method 40 provide for two-dimensional imaging of core biopsy samples. The resulting imaging data thus provides an area of pathologic tissue within the biopsy sample. According to another aspect of the disclosure, FIG. 4 illustrates a three-dimensional optical pathology system 58, which can provide for three-dimensional imaging of core biopsy samples. The resulting imaging data thus indicates a volume of pathologic tissue within a core biopsy sample, which may be helpful to determine whether the sample is adequate for proper tumor subtyping and genetic analyses.

As shown in FIG. 4, the system 58 can include a scaffold 86 defining a central chamber 88 and outlet channels 90, a plurality of LEDs 92 circumferentially arranged along the scaffold to uniformly light the central chamber 88, a camera 94 positioned at each outlet channel 90, and a lens 96 and filter 98 positioned between each outlet channel 90 and each camera 94. The system 58 can be a substantially portable "table-top" device and can be sized, for example, to fit on a rolling cart (not shown) to enable movement of the system 58 between procedure suites. The LEDs 92 and the cameras 94 can be in communication with and controlled by a computer 102 including a processor 104. Also, the LEDs 92 and the cameras 94 can be connected to the computer 102 via removable connectors 103 so that the system 58 can be used with different computers 102 in different procedure suites.

In some configurations, the scaffold 86 can be plastic and can house a cuvette 96 containing a core biopsy sample within its central chamber 88. The LEDs 92 can emit a specific wavelength based on the optical imaging agent used, thus causing the optical imaging agent to generate light in the form of fluorescence, autofluorescence, bioluminescence, Cerenkov luminesce or other methods. For example, in one configuration, the LEDs 92 can be 780 nm NIR LEDs to be used with optical imaging agents that fluoresce or otherwise emit light under that wavelength. The LEDs 92 can provide uniform NIR illumination emitted toward the core biopsy sample.

Emitted light from the core biopsy sample (e.g., as a result of the NIR excitation light from the LEDs 92) can pass through the outlet channels 90, be focused by the lenses 96, filtered by the filters 98 (e.g., NIR bandpass filters), and imaged by the cameras 94. The cameras 94 can be CCD cameras optimized for the excitation source's spectrum (in this configuration, the NIR spectrum). In one configuration, the cameras 94 are high-temporal and high-spatial resolution 12-bit NIR CCDs. The cameras 94 can thus be configured to capture sample optical images following excitation light emission by the LEDs 92. Additionally, in one configuration, the two outlet channels 90 and, thus, two the cameras 94, are each spaced about 180 degrees apart. As a result, the system 58 can acquire volumetric NIR data from core biopsy samples.

The computer 102 can control camera, light emission, and image display functions. More specifically, each computer 102 used with the system 58 can include a processor 104 configured to control the LEDs 92, collect imaging data from the cameras 94, analyze imaging data (for, for example, sample optical intensity), display imaging data or outputs indicative of the analysis, and/or perform other operations (e.g., by executing a software program stored on the computer 102). The computer 102 may perform the above operations, for example, in response to a user input initiating imaging data collection.

Figure 5:
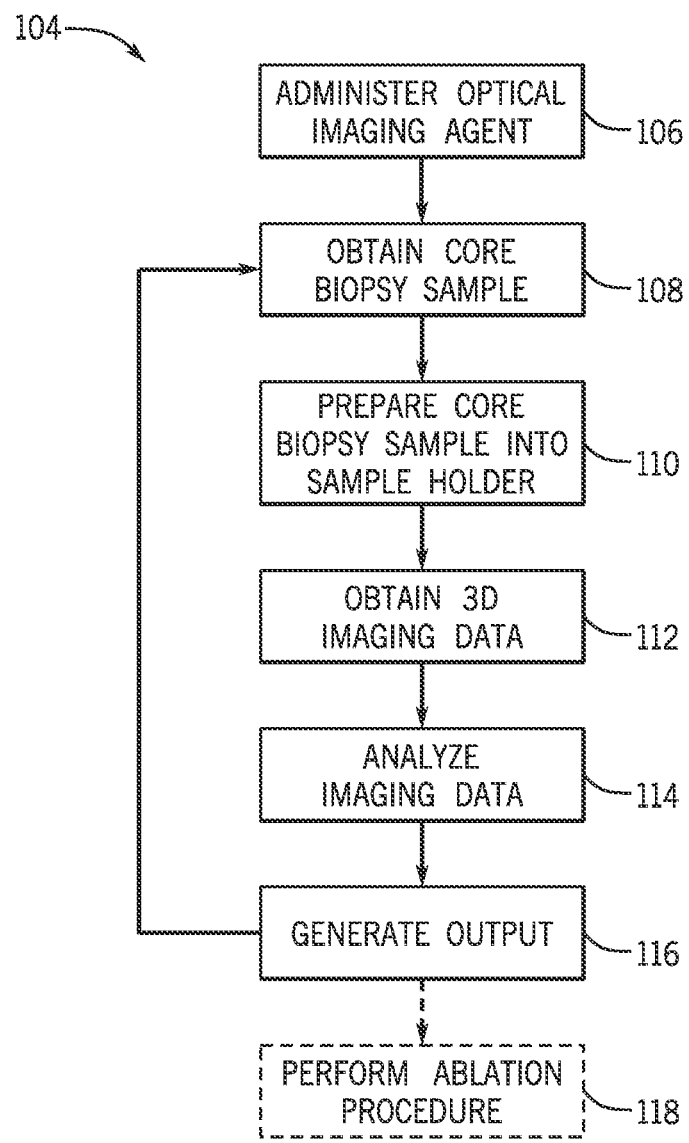
FIG. 5 illustrates a three-dimensional point-of-care imaging method according to one aspect of the disclosure.

FIG. 5 illustrates a three-dimensional point-of-care imaging method 104 according to one aspect of the disclosure, for use with the system 58. Generally, the method 104 includes administering an optical imaging agent to a subject (process block 106) and obtaining a core biopsy sample (process block 108). The extracted biopsy sample is then placed into the central chamber 88 (process block 110) and imaging data of the biopsy sample is obtained (process block 112). Once data acquisition is complete, the imaging data is analyzed (process block 114) and an output indicative of the analysis is generated (process block 116). The method (that is, process blocks 108-116) may be repeated for multiple biopsy samples. Additionally, in some configurations, following output generation at process block 116, an operator may perform an ablation procedure in an area from where the core biopsy sample was collected (process block 118).

More specifically, process block 106 includes administering an optical imaging agent to a subject and waiting for the optical imaging agent to reach the target pathologic tissue. In some configurations, this waiting period may take minutes, hours, or days. Additionally, in configurations where pathologic tissue images differently in the optical spectrum than normal tissue without the addition of an optical imaging agent, this step may be eliminated. At process block 108, a biopsy sample is obtained using imaging guidance, such as US or CT guidance. At process block 110, the biopsy sample can be extracted from the biopsy needle and prepared in a cuvette, for example, with a fixative solution, then placed into the central chamber 88.

At process block 112, the computer 102 collects three-dimensional imaging data of the biopsy sample. Three-dimensional imaging data may refer to data collected from multiple angles. For example, an operator can provide input to the computer 102, directing the computer 102 to initiate imaging data collection. In response to this input, the computer 102 initiates excitation light output toward the sample (e.g., via the LEDs 92), then operates the cameras 94 to collect imaging data of light emitted from the sample in response to the excitation light.

In some configurations, the imaging data can include raw imaging data or processed imaging data, such as an optical intensity measurement. For example, for each imaging angle, optical intensity measurements are measured by drawing a region of interest within a collected projected 12-bit image of the sample and calculating a mean pixel intensity of the region of interest (e.g., using an image analysis software package). Additionally, the optical intensity can be normalized by dividing the mean pixel intensity by the exposure time of the image. In some configurations, a maximum optical intensity from the region of interest is also determined. Additionally, in some configurations, image processing techniques may be applied to the imaging data, including scatter reduction techniques (such as angular 'memory-effect' for speckle correlations and an autocorrelation method). The imaging data can be stored on the computer 102 or other appropriate medium so that the imaging data can be later retrieved and analyzed.

At process block 114, the imaging data is analyzed by the computer 102 (e.g., via a specific software program) and/or by an operator (such as an interventional radiologist or surgeon). The purpose of the analysis at process block 114 is to determine (1) whether the imaging data indicates presence of the optical imaging agent in the biopsy sample (thus distinguishing pathologic tissue from non-pathologic tissue), (2) how much pathologic tissue is in the biopsy sample, and (3) whether the architectural integrity of the pathologic tissue within the sample is sufficient to render a histopathological diagnosis. More generally, the purpose of the analysis is to determine whether the biopsy sample is sufficient to avoid a repeat biopsy.

For example, analysis can include calculating the geometric mean of images acquired by the cameras 94. The resultant calculated image can undergo automated segmentation based upon a pixel intensity cutoff algorithm to generate statistics on the size and intensity of the largest contiguous volume of light emitting tissue. This data can then be compared to an index of biopsy sample quality to quantitatively measure pathologic tissue amount (e.g., as intensity) and architectural integrity (e.g., as largest contiguous dimension). The index may be a previously generated index stored on the computer 102 or accessed from a remote storage medium by the computer 102.

At process block 116, the computer 102 can generate and display (e.g., via a display screen) one or more outputs of the analysis, such as numerical optical measurements, volumetric measurements, such as pathologic tissue volume or architecture, status symbols indicating that the measurement is sufficient or insufficient, potential histologies, and/or one or more optical images of the biopsy core sample. The images can be displayed to allow for qualitative assessment of the sample by the proceduralist and pathologist.

The method 104 can not only indicate the presence of pathologic tissue in a biopsy sample, but can also provide a real-time indication of inhomogeneous tumor distribution in the biopsy sample and/or irregular core biopsy sample geometry. Thus, the method 104 can provide real-time guidance concerning whether additional samples should be acquired. Accordingly, process blocks 108-116 may be repeated to obtain multiple biopsy samples from the same or a new biopsy needle position based on the output generated at process block 116. Furthermore, the generated output at process block 116 can guide a pathologist in deciding where to obtain sections within a core biopsy sample, for example for frozen-section specimens or microscopic analysis of pathologic tissue.

Additionally, in some configurations, following output generation at process block 116, an operator can perform an ablation procedure at process block 118. For example, the method 104 can be used to determine proper introducer needle position at or within the pathologic tissue. When output indicates that a sample taken at that needle position contains pathologic tissue, an ablation probe, such as a microwave antenna, can be inserted through the introducer needle to perform, for example, microwave or radiofrequency ablation. The method 104 (or at least process blocks 108-118) may be repeated to ensure the pathologic tissue, in its entirety, is sufficiently burned via the ablation procedure.

In light of the above, aspects of the disclosure provide systems and methods for evaluating core biopsy specimens in interventional radiology suites. The present systems are consistent with the minimally invasive nature of such interventional radiology procedures. By using the systems in conjunction with an optical imaging agent, the systems non-destructively detect pathologic tissue in specimens ex-vivo by bed-side optical measurement. Unlike point of care cytologic evaluations, OMI of tissue light emission within core specimens is virtually instantaneous. Additionally, the three-dimensional system provides many desirable specifications for diagnostic imaging, such as rapid image reconstruction and automated imaging analysis, including volume segmentation, and optical volume quantitation.

The above-described systems and methods can also reduce sampling error and, thus, mitigate the clinical issue of false negative biopsies. In some cases, the systems and methods may also reduce overall procedure time by improving operator confidence in biopsy needle positioning and reducing the tendency of operators to obtain numerous core biopsy samples (i.e., due to uncertainty that each sample will contain pathologic tissue). Moreover, the improved operator confidence can enable sampling smaller pathologies, thereby allowing physicians to provide a diagnosis and appropriate management plan to patients earlier in the course of disease.

The above-described systems and methods may also be used beyond intra-procedural assessment of biopsy sample adequacy for other ex vivo tissue analyses. For example, the ability to automatically localize tumor within a tissue sample via the above-described systems and methods may be incorporated into cryostat machines for targeted tissue slicing of percutaneous or surgical biopsy specimens. This approach could optimize evaluation of tumor-containing sections and minimize unnecessary analysis of normal parenchyma. Likewise, volumetric analysis of tissue specimens during tumor resection surgeries could be performed in near real-time to provide surgeons with a preliminary assessment of tissue margin positivity.

The present invention has been described in terms of one or more preferred embodiments, and it should be appreciated that many equivalents, alternatives, variations, and modifications, aside from those expressly stated, are possible and within the scope of the invention.

The invention claimed is:

1. A three-dimensional optical pathology system for analyzing an ex vivo tissue sample, the three-dimensional optical pathology system comprising:
   a scaffold defining a hollow central chamber and two outlet channels, wherein the hollow central chamber is configured to receive the ex vivo tissue sample;
   a plurality of excitation sources positioned along the scaffold and configured to emit light into the hollow central chamber;
   two cameras, wherein a camera is positioned at each of the two outlet channels and configured to acquire imaging data following light emission into the hollow central chamber; and
   a computer in communication with the plurality of excitation source and the two cameras, the computer including a processer configured to:
      activate the excitation sources to deliver the light to the ex vivo tissue sample,
      collect the imaging data from the two cameras,
      analyze the imaging data to distinguish pathologic tissue from non-pathologic tissue within the ex vivo tissue sample and determine a volumetric measurement of the pathologic tissue within the ex vivo tissue sample, and
      display an indication of the volumetric measurement.

2. The three-dimensional optical pathology system of claim 1, wherein the imaging data includes optical intensity, and analyzing the imaging data includes comparing the optical intensity to a threshold intensity.

3. The three-dimensional optical pathology system of claim 1, wherein the volumetric measurement includes one of pathologic tissue volume and pathologic tissue architecture.

4. The three-dimensional optical pathology system of claim 3, wherein the indication includes one of the volumetric measurement, a status symbol indicating presence of the pathologic tissue in the biopsy tissue sample, and images of the ex vivo tissue sample.

5. The three-dimensional optical pathology system of claim 1, wherein the two outlet channels are positioned about 180 degrees apart, across the hollow central chamber.

6. The three-dimensional optical pathology system of claim 1 and further comprising a lens and a filter positioned between each of the two outlet channels and respective ones of the two cameras.

7. The three-dimensional optical pathology system of claim 1, wherein the hollow chamber is configured to receive a cuvette containing the ex vivo tissue sample.

8. The three-dimensional optical pathology system of claim 1, wherein the imaging data indicates light emitted by an optical imaging agent within the ex vivo tissue sample in response to light emission into the hollow central chamber.

* * * * *